(12) United States Patent
Teitelbaum (10) Patent No.: US 10,022,251 B2
(45) Date of Patent: Jul. 17, 2018

(54) FLOW DIVERSION DEVICE (71) Applicant: ANCHOR ENDOVASCULAR, INC., Santa Monica, CA (US)

(72) Inventor: George P. Teitelbaum, Santa Monica, CA (US)

(73) Assignee: George P. Teitelbaum, Santa Monica, CA (US)

( * ) Notice: Subject to any disclaimer, the term of this patent is extended or adjusted under 35 U.S.C. 154(b) by 192 days.

(21) Appl. No.: 14/959,830

(22) Filed: Dec. 4, 2015

(65) Prior Publication Data
US 2016/0158038 A1 Jun. 9, 2016

Related U.S. Application Data

(60) Provisional application No. 62/088,379, filed on Dec. 5, 2014.

(51) Int. Cl.
*A61F 2/06* (2013.01)
*A61F 2/90* (2013.01)
(Continued)

(52) U.S. Cl.
CPC .................. *A61F 2/90* (2013.01); *A61F 2/01* (2013.01); *A61F 2/07* (2013.01); *A61F 2/013* (2013.01); *A61F 2/962* (2013.01); *A61F 2002/011* (2013.01); *A61F 2002/016* (2013.01); *A61F 2002/061* (2013.01); *A61F 2002/072* (2013.01);
(Continued)

(58) Field of Classification Search
CPC .... A61F 2/01; A61F 2/013; A61F 2/07; A61F 2/90
See application file for complete search history.

(56) References Cited

U.S. PATENT DOCUMENTS

| 6,245,012 | B1 * | 6/2001 | Kleshinski | ............... A61F 2/013 623/1.11 |
| 2008/0200979 | A1 * | 8/2008 | Dieck | ................... A61F 2/0077 623/1.44 |

(Continued)

FOREIGN PATENT DOCUMENTS

DE 19509464 C1 * 6/1996 ............... A61F 2/01

OTHER PUBLICATIONS

EV3, Introducing a New Treatment Method for Brain Aneurysms: Pipeline® Embolization Device, 2011, 4 pp.
(Continued)

*Primary Examiner* — Ashley Fishback
(74) *Attorney, Agent, or Firm* — Stoel Rives LLP (57) ABSTRACT

A flow diversion device for the treatment of intracranial aneurysms and other medical conditions is disclosed. The flow diversion device may include a generally tubular wire stent frame formed from a plurality of zig-zag shaped wire elements that are coupled together. The device further includes a base layer of graft material coupled to the wire stent frame and surrounding at least a portion thereof, the wire stent frame maintaining the base layer in an open condition. In some embodiments, the base layer may be formed of porous graft material having a plurality of pores formed thereon to provide a passageway for a small blood flow to maintain the long term patency of important small side branches, while also reducing blood flow to the aneurysm to promote occlusion and avoid potential rupture.

19 Claims, 5 Drawing Sheets

(51) Int. Cl.
*A61F 2/01* (2006.01)
*A61F 2/07* (2013.01)
A61F 2/962 (2013.01)
A61F 2/82 (2013.01)
A61F 2/848 (2013.01)

(52) U.S. Cl.
CPC ... *A61F 2002/075* (2013.01); *A61F 2002/823* (2013.01); *A61F 2002/825* (2013.01); *A61F 2002/8486* (2013.01); *A61F 2210/0076* (2013.01); *A61F 2230/0006* (2013.01); *A61F 2230/0008* (2013.01); *A61F 2230/008* (2013.01); *A61F 2230/0076* (2013.01); *A61F 2250/0023* (2013.01)

(56) References Cited

U.S. PATENT DOCUMENTS

2013/0345627 A1* 12/2013 Angel .................. A61F 2/01
 604/93.01
2014/0249620 A1* 9/2014 Carman .................. A61F 2/07
 623/1.39

OTHER PUBLICATIONS

Byrne, JV et al.: "Flow Diverters in the Management of Intracranial Aneurysms: A Review," *EJMINT*, Jun. 22, 2012, 22 pp.
Covidien, "Flow Diversion," www.ev3.net/neuro/intl/flow-diversion/, 2013, 5 pp.
Wahkloo, AK: "Surpass™ Flow Diverter: Scent Trial Update," SVIN, Hollywood FL, Nov. 9, 2014, 21 pp.

* cited by examiner

FLOW DIVERSION DEVICE

RELATED APPLICATION DATA

This application is a nonprovisional of and claims the benefit under 35 U.S.C. § 119(e) of U.S. Provisional Patent Application No. 62/088,379, filed Dec. 5, 2014, the disclosure of which is incorporated by reference herein in its entirety.

TECHNICAL FIELD

The field of the present disclosure relates generally to medical devices, and in particular, to flow diversion devices that may be used for treatment of wide-neck and fusiform aneurysms.

BACKGROUND

Flow diversion devices, such as the Pipeline embolization device, the Surpass flow diverter, and the Silk flow diverter, are stent-like devices composed of tightly-braided, thin wire elements typically used for the treatment of intracranial aneurysms. These devices are employed endovascularly to treat aneurysms by diverting blood flow away from the aneurysm to induce aneurysm thrombosis, which helps prevent rupture of the aneurysm and may eventually result in the gradual shrinkage and occlusion of the aneurysm. In addition, when used for fusiform aneurysms (i.e., aneurysms with no definable neck), the flow diversion device may promote reconstruction of a smooth endothelial covered channel in continuation with the parent artery. While the flow diversion device directs blood away from the aneurysm, the thin-wire braided design allows modest through-flow of blood to maintain the patency of important small arterial side branches adjacent to the treated aneurysm.

Large intracranial aneurysms (which range in diameter from 10-25 mm) and particularly giant intracranial aneurysms (those greater than 25 mm in diameter) frequently have a wide-neck (dome-to-neck diameter ratio of less than 2) or are fusiform. Typically, large and giant aneurysms have poor occlusion, rupture and survival rates regardless of the form of therapy (e.g., open brain surgery or other endovascular techniques) used to treat them. The use of finely braided stent devices to divert blood flow away from aneurysms has yielded promising treatment results compared to open surgery and other conventional endovascular techniques, such as coil embolization with or without the assistance of an endovascular stent or balloon remodeling.

DETAILED DESCRIPTION OF EXAMPLE EMBODIMENTS

With reference to the drawings, this section describes particular embodiments and their detailed construction and operation. The embodiments described herein are set forth by way of illustration only and not limitation. The described features, structures, characteristics, and methods of operation may be combined in any suitable manner in one or more embodiments. In view of the disclosure herein, those skilled in the art will recognize that the various embodiments can be practiced without one or more of the specific details or with other methods, components, materials, or the like. For the sake of clarity and conciseness, certain aspects of components or steps of certain embodiments are presented without undue detail where such detail would be apparent to those skilled in the art in light of the teachings herein and/or where such detail would obfuscate an understanding of more pertinent aspects of the embodiments.

The present inventor has recognized some disadvantages relating to current flow diversion devices. For example, one disadvantage is that the very fine braids in the wire mesh tube of current devices make it challenging to deliver the device intracranially, usually requiring larger diameter and stiffer microcatheters to advance the collapsed stent device to the target region of the affected artery. In some circumstances, these large bore, stiffer microcatheters may be unstable and lead to inadvertent displacement of the flow diversion device into the aneurysm cavity. Moreover, once in place, the construction of such stent devices may make their expansion somewhat difficult, which may cause undesired effects, such as: (1) leading to blockage of normal blood flow to part of the brain, thereby threatening a stroke, and (2) creating undesirable space between the outer surface of the stent and the blood vessel interior or intima, thereby permitting side branches to create an endoleak, which may result in the undesirable maintenance of flow into the aneurysm cavity.

Another disadvantage of such current flow diversion devices is that positional instability of the device during deployment may cause the device to unexpectedly kick back into the aneurysm. In addition, such current devices may also create a large metal burden for the treated artery, which may increase the risk for thromboembolic events and require prolonged therapy or treatment.

As further described in detail below, certain embodiments described herein may be capable of achieving various advantages, including one or more of the following: (1) providing a flow diversion device with a streamlined design to simplify endovascular introduction and decrease forces placed on the delivery catheter; (2) providing such a flow diversion device constructed to promote expansion of the device once in position for improved flow; and (3) providing a flow diversion device that effectively diverts blood away from an aneurysm while maintaining sufficient blood flow to maintain patency of arterial side branches adjacent the aneurysm treatment site. Additional aspects and advantages will be apparent from the following detailed description of example embodiments, which proceeds with reference to the accompanying drawings.

Collectively, FIGS. 1-14 illustrate various embodiments of a flow diversion device that may be used for the treatment of intracranial aneurysms and other medical procedures as further detailed below with reference to the figures. Generally, with reference to FIG. 1, the flow diversion device 100 is a stent-like device including a plurality of wire elements 105, where each individual element 105 is shaped in a zig-zag pattern and coupled to adjacent wire elements to form a general tube-shaped stent structure. The wire elements 105 hold open a thin base layer 135 and together form a support structure of the flow diversion device 100. An outer jacket 145 may surround the support structure formed of the wire elements 105 and the base layer 135, the jacket 145 being fused to the base layer 135 to provide added rigidity and maintain the tubular shape of the flow diversion device 100. As briefly mentioned previously, the flow diversion device 100 may be employed endovascularly to treat aneurysms by diverting blood flow away from the aneurysm to induce aneurysm thrombosis and for other suitable medical procedures. Additional details of these and other embodiments of the flow diversion device 100 are described herein with reference to the figures.

Figure 1:
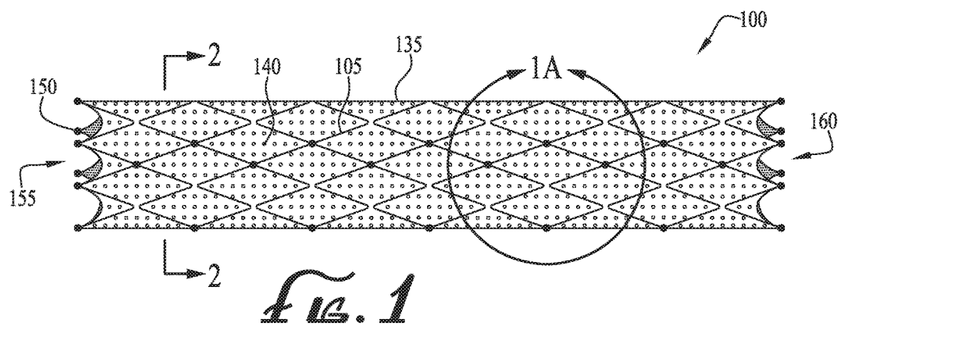
FIG. 1 illustrates an example flow diversion device according to one embodiment.
Figure 2:
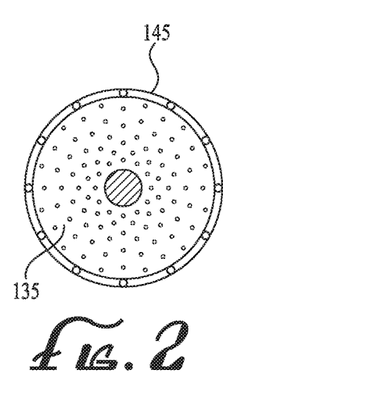
FIG. 2 is a cross-section view of the flow diversion device of FIG. 1.

With particular reference to FIGS. 1 and 2, the following sections describe additional details of the flow diversion device 100 and the components thereof. As briefly described previously, the flow diversion device 100 includes a plurality of wire elements 105 coupled together to form a generally tubular-shaped, self-expanding stent structure. In some embodiments, the wire elements 105 may be composed of a metallic material exhibiting shape memory/superelasticity qualities, such as nitinol (a nickel-titanium alloy), Elgiloy (a cobalt, chromium, and nickel based alloy) or other suitable shape-memory alloys. In other embodiments, the wire elements 105 may instead be composed of other suitable materials, including non-metallic materials, capable of creating the tubular stent structure.

Figure 1A:
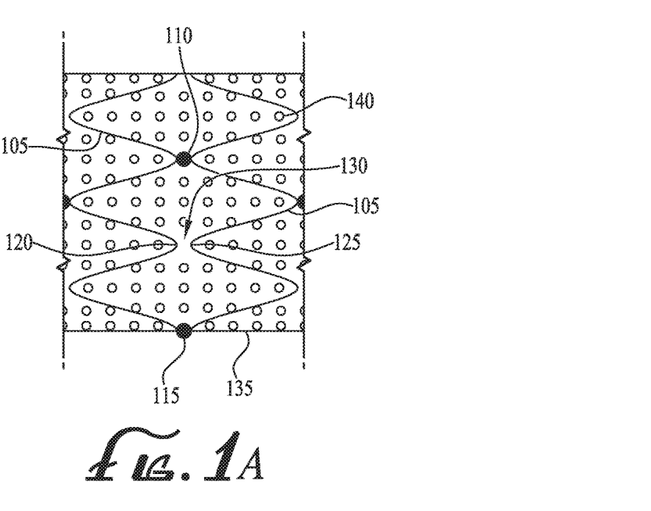
FIG. 1A is an enlarged view of a portion of the flow diversion device of FIG. 1.

In some embodiments, the wire elements 105 may be coupled together, such as via a welding process, in a staggered or alternating pattern at one or more sites to create an "open cell" design capable of following sharp curves in blood vessels without kinking. For example, with particular reference to FIG. 1A, adjoining wire elements 105a and 105b may be welded at a first junction 110 and a second junction 115, leaving free at a central junction 130 a pair of ends 120, 125 of the respective wire elements 105a, 105b (i.e., the ends 120, 125 are not welded or otherwise attached to one another). In this configuration, the staggered welds between the adjacent wire elements 105a, 105b may help impart greater flexibility to the flow diversion device 100 without sacrificing the overall stability. It should be understood that while the embodiment of the flow diversion device 100 in FIG. 1 illustrates a welding pattern at alternating junctions, the wire elements 105 may instead be attached/linked in any one of a variety of suitable patterns. For example, in other embodiments, the wire elements 105 may be attached at every junction to increase stability, or may be attached in a non-alternating fashion at select junctions for additional flexibility.

In some embodiments, the flow diversion device 100 may use or include few wire elements 105 to minimize resistance while the device 100 is advanced to a target site. In addition, the diameter of each of these wire elements 105 is selected to ensure each wire element 105 possesses sufficient expansive force once the flow diversion device 100 is deployed at the target site, thereby decreasing the chance of incomplete expansion, and in turn, avoiding a dangerous blockage of blood flow. For example, in one embodiment, the diameter of each wire element 105 may be equal to or less than 0.005 inches to create a flow diversion device 100 with sufficient stiffness, flexibility, and proper expansile forces to help ensure that the flow diversion device 100 is securely fixed to the target vessel site to cover the neck of an aneurysm or provide a flow pathway through a fusiform aneurysm as further described with particular reference to FIGS. 6A and 6B. In other embodiments, the diameter of each wire element 105 may be less than 0.010 inches.

With reference to FIGS. 1 and 2, the flow diversion device 100 includes a tubular, ultra-thin base layer 135 of graft material, such as polytetrafluoroethylene (PTFE), or other suitable graft fabric to promote the flow diversion characteristics of the device 100. The base layer 135 and the stent frame formed of wire elements 105 may be attached to one another by any suitable means, such as via suture material, crimping, adhesive, or perhaps sealing one ultra-thin layer of graft material to another with the wire stent structure contained between the two layers. To help assure flow to and long term patency of important small side branches frequently found along intracranial arteries, the graft material of the base layer 135 may include a plurality of minute perforations/pores 140 spaced apart on the base layer 135 to allow a small amount of blood flow through to the side branches. The perforation/pores 140 may be created mechanically, by using laser energy, or by any other suitable means. The size and shape of the perforations 140 may be designed so as to promote increased through-flow "on demand," (e.g., the pores allow greater flow to patent side branches but afford less flow to an aneurysm) without being too large so as to reduce the structural integrity of the base layer 135.

In some embodiments, the perforations/pores 140 may be designed and cut on the base layer 135 such that the perforations/pores 140 enlarge or change shape with increased flow demand. For example, the perforations/pores 140 may be half-circle incisions or slits, in a similar pattern as is typically found in a flag. As the blood flow against the base layer 135 increases, the half-circle incisions allow a flap of graft fabric to fold away (relative to the direction of blood flow) and prevent excess billowing of the base layer 135 (which might result in its tearing or dislodgement). Preferably, in the absence of any special characteristics of the perforations/pores 140, the porous graft material of the base layer 135, nonetheless, provides flow diversion by greatly inhibiting flow into an aneurysm sac, causing its gradual shrinkage and occlusion, while still providing diminished but sufficient flow to maintain patency of side branches.

As illustrated in FIG. 1, the flow diversion device 100 may include radiopaque markers 150 at both the proximal 155 and distal 160 ends. Using fluoroscopy, the radiopaque markers 150 allow an operator to view a position of the flow diversion device 100 and to determine whether the flow diversion device 100 has properly engaged the interior wall of the blood vessels or other lumen. In other embodiments, the wire elements 105 may also (or alternatively) include radiopaque material so that the periphery/boundary of the stent frame may be viewed.

With particular reference to FIG. 2, the base layer 135 of graft material may be fused with an outer jacket 145 to maintain the overall shape of the flow diversion device 100. In some embodiments, the jacket 145 may be made of polyurethane or other suitably strong, lightweight, and flexible polymer.

Figure 3:
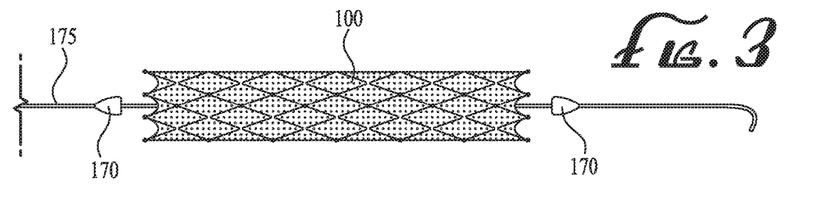
FIGS. 3, 4, and 5 illustrate an example assembly and delivery of the flow diversion device of FIG. 1 via a catheter and pusher wire according to one embodiment.
Figure 4:
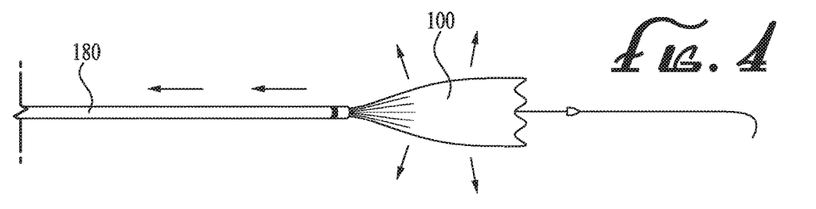
Figure 5:
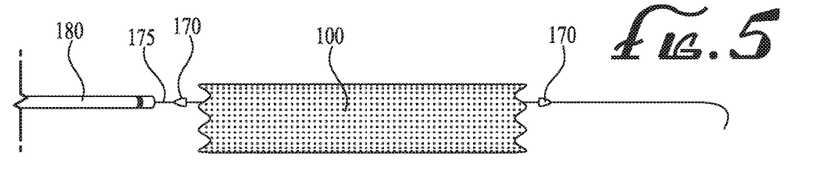
Figure 6A:
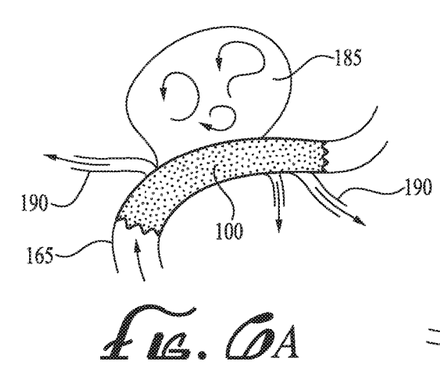
FIGS. 6A and 6B illustrate schematic views of the flow diversion device in position at a delivery site for treatment of an aneurysm.

FIGS. 3-5 illustrate example embodiments for delivering the flow diversion device 100 to a blood vessel or other lumen 165 (see FIG. 6A). With particular reference to FIGS. 3 and 4, the flow diversion device 100 may be advanced in a compressed state between two metal bumpers 170 on a pusher/delivery wire 175 through a delivery catheter 180. Once the flow diversion device 100 is pushed to the target segment of the intracranial artery or other lumen 165 via the catheter 180, the catheter 180 may be withdrawn to allow the device 100 to expand at the target site. In other embodiments, the flow diversion device 100 may instead be mounted on a pusher wire and once the device is expanded/deployed at the target site, it can then be detached from the pusher wire by electrolytic or mechanical means. Both of the aforementioned methods of device delivery and deployment may, up to a certain point, allow retrieval of the flow diversion device if the deployed position is unsatisfactory.

Figure 6B:
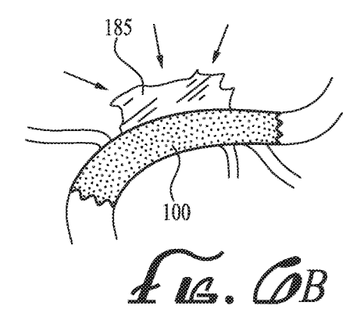

FIGS. 6A and 6B schematically illustrate an example flow diversion process of the deployed device 100 when used to treat intracranial aneurysms. With reference to FIGS. 6A and 6B, the flow diversion device 100 is positioned adjacent an intracranial aneurysm 185 (such as a large or giant, wide-neck or fusiform intracranial aneurysm). When in position, the porous graft material of the base layer 135 reduces/inhibits blood flow into the aneurysm 185 thereby causing it to gradually occlude over time (as illustrated in FIG. 6B). Since the graft material is porous, a small amount of blood may flow into the aneurysm 185, but this flow is sufficiently small such that the aneurysm will likely not continue growing. Moreover, the small amount of flow across the graft material remains sufficient to maintain patency of nearby side branches 190. In some treatments, for approximately a week prior to and 3-6 months following the deployment of the described flow diversion device 100, the patient may be treated with dual anti-platelet therapy (such as aspirin and clopidogrel (Plavix)). A follow-up cerebral angiogram may be performed at 6 and 12 months following device deployment to assess for aneurysm shrinkage and occlusion. If the aneurysm is fully occluded and determined to be no longer problematic, the device 100 may be removed. In other instances, the device 100 may be left in position permanently to avoid potential future problems.

FIGS. 7-14 collectively illustrate various other embodiments for medical procedures and process utilizing a similar concept of a wire mesh frame and a graft material base layer as described above with reference to the flow diversion device 100 of FIGS. 1-6. The following describes additional detail of these embodiments.

Figure 7:
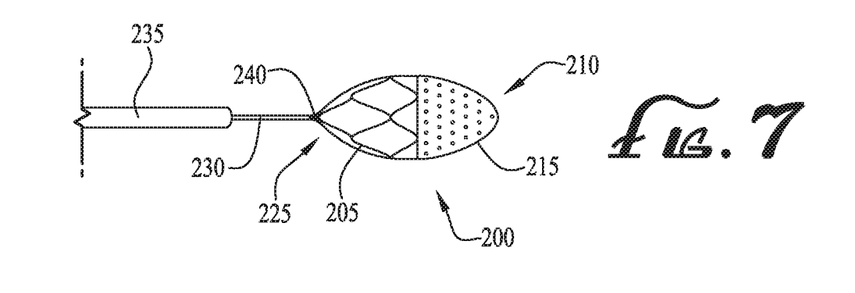
FIGS. 7 and 8 collectively illustrate an example of the flow diversion device, according to another embodiment.
Figure 8:
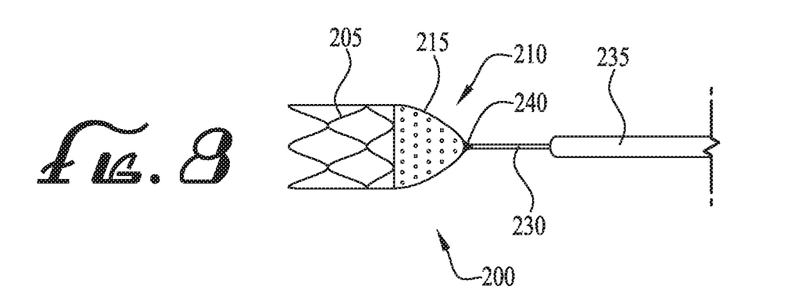

FIGS. 7 and 8 illustrate example embodiments of an inferior vena cava (IVC) filter 200 for helping prevent pulmonary emboli. With reference to FIG. 7, the IVC filter 200 may include a plurality of wire elements 205 each having a zig-zag shape, where each element 205 is welded or otherwise coupled to an adjacent element to form a stent frame in a similar fashion as described with respect to wire elements 105 of flow diversion device 100. The wire elements 205 at a distal end 210 of the IVC filter 200 may be gathered together and welded or otherwise mechanically constrained together to create a closed, conical shape at the distal end 210. A porous base layer 215 of graft material (e.g., PTFE, polyurethane or other suitable material) having perforations 220 which may range in diameter from 25 microns to 100 microns may be attached or otherwise mounted to the mesh structure of wire elements 205 along at least the distal end 210 portion. The proximal end 225 of the IVC filter 200 includes a tubular configuration that may exert sufficient expansive force so as to act as an endovascular "anchor."

With particular reference to FIG. 7, in some embodiments, the proximal end 225 of the IVC filter 200 may be attached to a guidewire 230 which, in conjunction with a delivery catheter 235, may be used to position the IVC filter 200 in the inferior vena cava. Positioning the guidewire 230 at the proximal end 225 may be useful for inserting the IVC filter via the femoral vein so that the porous graft material is in the proper location relative to the direction of blood flow in the interior vena cava. With reference to FIG. 8, in other embodiments, the distal end 210 of the IVC filter 200 may instead be attached to the guidewire 230 and delivered to the inferior vena cava, such as via the internal jugular vein. In both embodiments, the IVC filter 200 may be a temporary filter (where the proximal or distal wire could be used as a means for retrieval of the IVC filter 200), or may instead be a permanent IVC filter 200. In such embodiments where the IVC filter 200 is permanent, the IVC filter 200 may include a detachment zone 240 positioned between the introduction guidewire 230 and the IVC filter 200 for allowing detachment of the IVC filter 200 when desired. Alternatively, the guidewire 230 may be used to slide a recover/resheathing catheter over the IVC filter 200 and retrieve it if desired.

In use, the stent-like body (with a closed cell design) comprised of the welded wire elements 205 make the filter self-centering within the interior vena cava. In addition, the perforated graft material of the base layer 215 is positioned to accommodate blood flow and otherwise trap thromboemboli from the pelvis and/or lower extremities that could otherwise cause a fatal pulmonary embolus if it reached the lungs. Such an IVC filter 200 may be advantageous since PTE (pulmonary thromboemboli) is currently the third leading cause of death in the United States.

Figure 9:
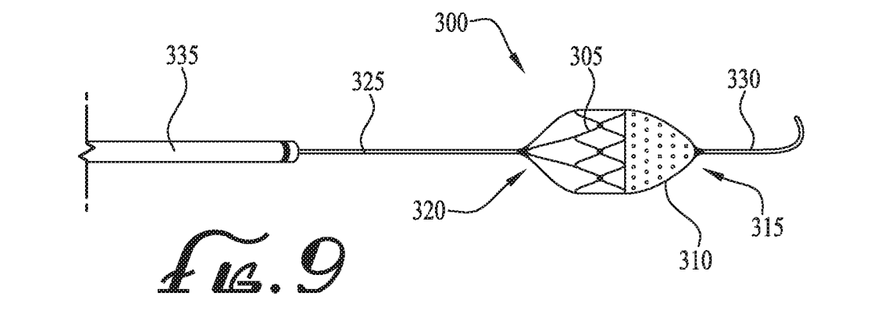
FIG. 9 illustrates an example embodiment of the flow diversion device that may be used for carotid and coronary bypass grafting.

FIG. 9 illustrate an example embodiment of an anchor-filter device 300 that may be used for carotid and coronary and bypass graft angioplasty and stenting. With reference to FIG. 9, the anchor-filter device 300 may include a similar stent-like scaffold made of welded wire elements 305 and a porous base layer 310 attached to a distal end 315 of the anchor-filter device 300 in a similar fashion as described with reference to the IVC filter 200 of FIGS. 7 and 8. The proximal end 320 of the anchor-filter device 300 may be attached to a guidewire 325 (such as a 0.014" to a 0.018" proximal working wire). The guidewire 325 may run the length of the anchor-filter device 300 and emerge distally as a short shapeable wire extension 330 for accommodating navigation past a stenosis and into the more normal distal arterial segment while the anchor-filter device 300 is in a collapsed state in a microcatheter 335 (approximately 3-F outer diameter). Such an anchor-filter device 300 may help prevent distal debris embolization arising from percutaneous transluminal angioplasty (PTA) and stenting of an atherosclerotic vessel by filtering procedural debris. Once the procedure is completed, the anchor-filter device 300 is collapsed by a retrieval catheter 335 slid up along the proximal guide wire 325, whereupon the device 300 would be removed from the artery.

In cases of extremely tortuous great vessel anatomy of the thoracic aortic arch (such as in the elderly and hypertensive), proximal access within the innominate or left common carotid artery could be established with a stiffer (e.g., ALZ) 7-F coronary guiding catheter, and then an approximately 2.8-F delivery microcatheter can be guided through the high-grade ICA stenosis over a 0.014" wire. This wire may then be removed and replaced with the anchor-filter device that would then be deployed in the upper cervical ICA. Here it would stabilize the working wire and then permit easier, more rapid catheterizations in thoracic arch tortuous anatomy by means of a bi- or tri-axial catheter system, and may potentially also be useful to prevent distal grumous embolization during angioplasty and stenting of stenotic coronary bypass grafts. Once debris are captured at the conclusion of PTA and stenting, the filter device is re-captured by advancing an approximately 2.8F recovery catheter over the working wire (which was used to also introduce PTA balloon catheters and stent devices) and collapsing the filter.

Figure 10:
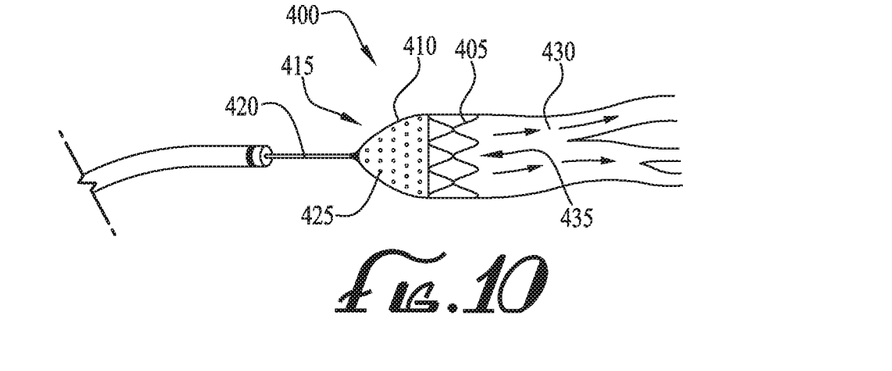
FIG. 10 illustrates an example embodiment of a flow diversion device with a flexible hypotube for delivering embolic particles through the flow diversion device.

In still other embodiments, with reference to FIG. 10, the combination of perforated graft material and stent-like scaffold may be used for a reverse or retrograde filter device 400 to provide a mechanism for infusing chemotherapeutic agent-soaked embolic particles or minute $Y^{90}$ radio-embolization particles. With reference to FIG. 10, the retrograde filter device 400 may include a wire mesh scaffold comprising a plurality of wire elements 405 attached in a similar fashion as described previously with respect to the devices 100, 200, 300. In addition, the retrograde filter device 400 further includes a base layer 410 of perforated graft material (e.g., PTFE or polyurethane) mounted or otherwise attached around a proximal end 415 of the wire mesh frame of the retrograde filter device 400.

The proximal end 415 of the wire mesh frame comprising wire elements 405 is mounted to a flexible hypotube 420 having an inner diameter of approximately 0.014" or any other inner diameter suitable to allow the injection of particles (e.g., Biospheres, polyvinyl alcohol particles, $Y^{90}$Therasphere particles) for radioembolization. In the case of radioembolization, backflow of the injected particles from the intra-arterial point of embolization may cause the particles to flow into a vital collateral channel serving the small bowel or stomach (e.g., the right gastric artery-in this case the radioactive Y90 particles could induce a nonhealing ulcer of the gastric mucosa). To avoid such problematic backflow, the proximal end 415 of the wire mesh stent has a conical shape and the perforations 425 on the graft material of the base layer 410 are appropriately sized to allow antegrade flow within the target vessel 430, but not to allow the backflow of injected particles, thus avoiding nontarget embolization into more proximal branch or collateral vessels. As illustrated in FIG. 10, the distal end 435 of the wire mesh stent may be open and have a cylindrical or tubular shape, the distal end 435 not being entirely covered with the graft material of the base layer 410. Accordingly, the distal end 435 fully expands to bear against the target vessel's inner walls and maintain the retrograde filter device 400 firmly in position.

Figures 11, 12, 13:
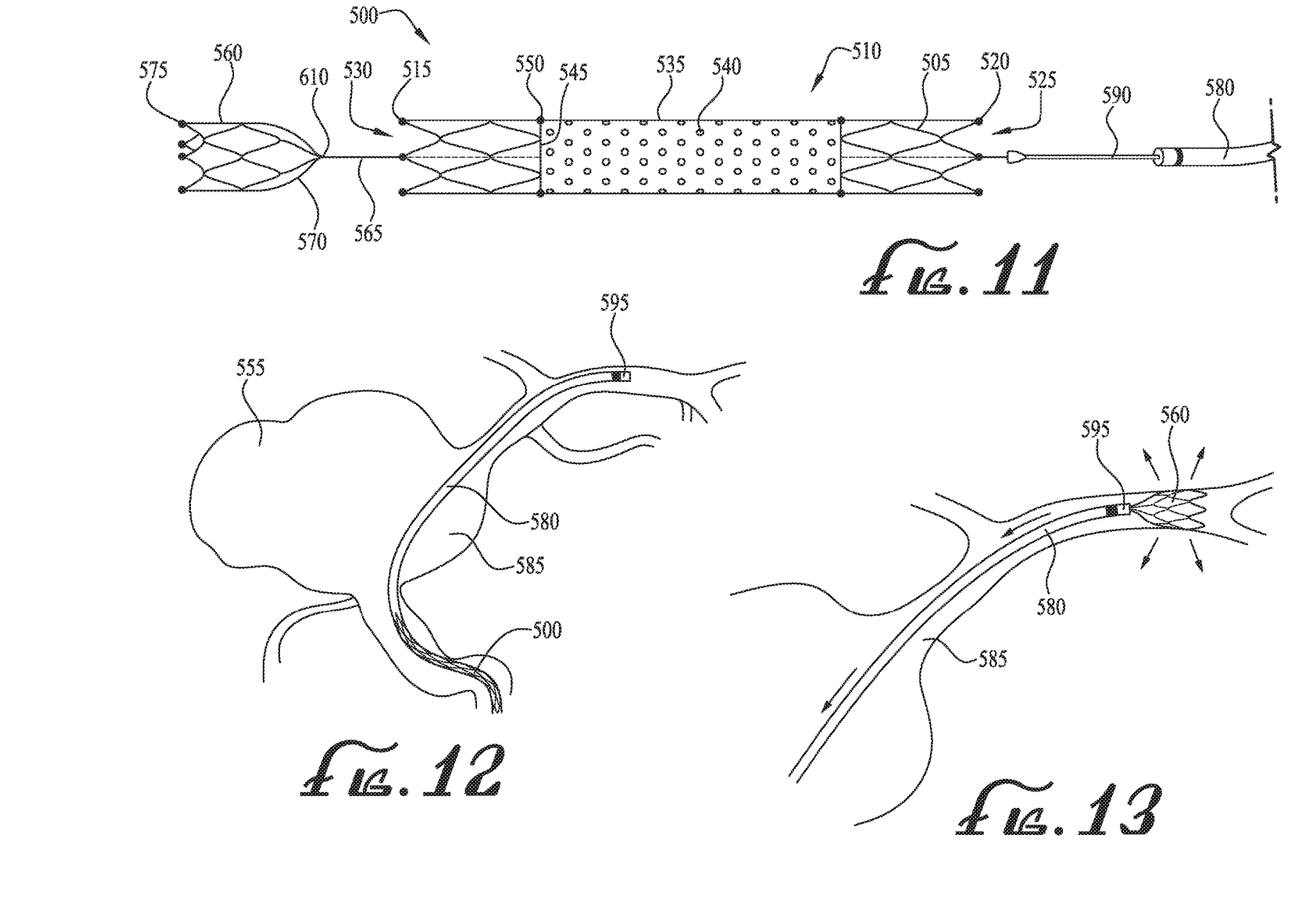
FIG. 11 illustrates an example embodiment of a flow diversion device with features for improving flow to larger side branches.
FIGS. 12, 13, and 14 illustrate an example delivery process for the flow diversion device of FIG. 11 to a treatment site.
Figure 14:
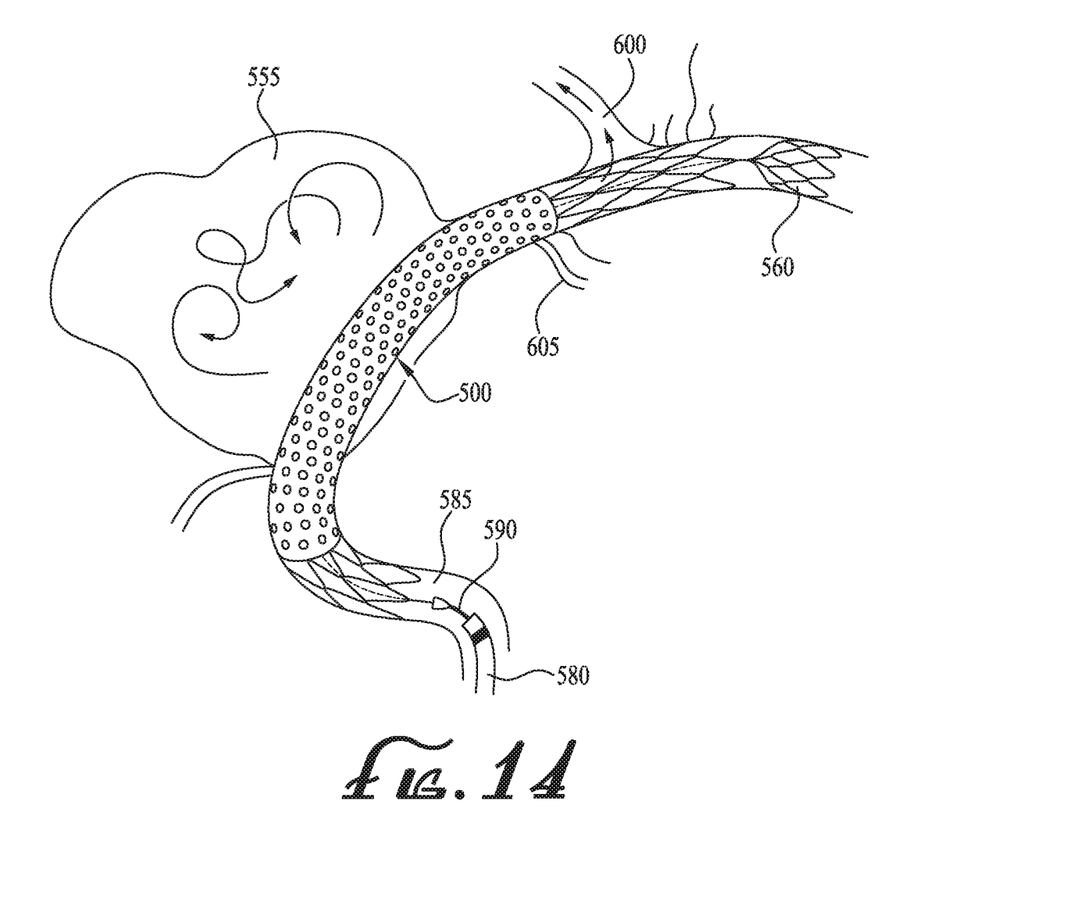

FIG. 11 illustrates another example embodiment of a flow diversion device 500 that may be used to divert blood flow away from an aneurysm 555, while also maintaining sufficient blood flow to maintain patency of large side branches 600 (see FIG. 14). With reference to FIG. 11, the flow diversion device 500 includes a self-expanding, partially open-cell stent frame 510 formed from a plurality of wire elements 505 coupled in a similar fashion as described with respect to the flow diversion device 100 of FIG. 1. In some embodiments, the flow diversion device 500 may include radiopaque markers 515, 520 on the wire elements 505 at both a proximal end 525 and a distal end 530 of the stent frame 510 to allow an operator to monitor a position of the flow diversion device 500 using fluoroscopy. In other embodiments, the wire elements 505 may also (or alternatively) include radiopaque material so that the periphery or boundary of the stent frame 510 may be monitored during the insertion and treatment procedure.

The flow diversion device 500 includes an ultra-thin base layer 535 of graft material, such as polytetrafluoroethylene (PTFE), or other suitable graft fabric that surrounds at least a portion of the stent frame 510, with the base layer 535 including a plurality of perforations/pores 540 formed thereon to help control blood flow to the treatment site. Preferably, the base layer 535 is positioned on a substantially central portion of the stent frame 510, leaving the proximal and distal ends 525, 530 free of the base layer 535. As is explained in additional detail below, the base layer 535 inhibits or reduces blood flow therethrough due to the relatively small size of the perforations 540, but the openness of the stent frame 510 and the proximal and distal ends 525, 530 allows for increased blood flow to large side branches 600 that may be adjacent the treatment site of the aneurysm 555. In some embodiments, a portion of the boundary 545 of the base layer 535 may include radiopaque markers/material 550 to allow an operator to precisely place the stent frame 510 at a particular treatment site and to ensure that blood flow away is directed away from the aneurysm 555 while also directing sufficient blood flow to large side branches adjacent the aneurysm 555 as further described in detail below with reference to FIGS. 12-14.

In some embodiments, the flow diversion device 500 may include an anchor stent 560 attached to a guidewire 565 and extending forwardly from the distal end 530 of the stent frame 510. With reference to FIG. 11, the anchor stent 560 is a generally tubular-shaped, self-expanding mesh structure similar in construction to the stent frame 510. The anchor stent 560 includes a plurality of connector struts 570 coalescing to a strut tip 610 at which a guidewire 565 is attached. In some embodiments, the anchor stent 560 may also include radiopaque markers 575 on an end opposite the connector struts 570. In use, the anchor stent 560 provides a means to secure in place the flow diversion device 500 to ensure proper treatment is provided for the aneurysm 555.

FIGS. 12-14 illustrate example embodiments for delivering the flow diversion device 500 to a target site for treating an aneurysm 555. With general reference to FIGS. 12-14, a delivery catheter 580 is advanced into the blood vessel 585 beyond the treatment site where the aneurysm 555 is located. As illustrated in FIG. 12, once the catheter 580 is in position, the flow diversion device 500 is advanced via a guidewire 590 through the catheter 580, the flow diversion device 500 being in a compressed state as it travels through the catheter 580. Once the flow diversion device 500 reaches the end 595 of the catheter 580, the anchor stent 560 extends outwardly from the end 595 and expands radially against an inner wall of the vessel 585 to stabilize the catheter 580 as illustrated in FIG. 13. Once the anchor stent 560 is fully expanded, the catheter 580 may be retracted away from the target site, wherein retracting the catheter 580 unsheathes the flow diversion device 500.

In one example deployment process, the guidewire 590 is held stationary while the catheter 580 is retracted, with the anchor stent 560 helping retain the flow diversion device 500 in position at the target site. With reference to FIG. 14, once the catheter 580 is fully retracted, the flow diversion device 500 is at the target position, with the base layer 535 adjacent the aneurysm 555 to divert blood flow away from the aneurysm 555 and cause the aneurysm 555 to occlude over time. In addition, as mentioned previously, the open proximal and distal ends 525, 530 of the stent frame 510 provide for increased blood flow to larger side branches 600 that may be near the aneurysm 555, and the perforations 540 on the base layer 535 provide sufficient flow for the smaller side branches 605.

When the treatment is complete and the flow diversion device 500 is ready for removal, the flow diversion device 500 may be resheathed by advancing the catheter 580 toward the proximal end 525 of the stent frame 510. As the catheter 580 moves forward, the flow diversion device 500 collapses into the catheter 580. Once the entire device 500 is sheathed in the catheter 580, the catheter 580, together with the device 500, may be removed.

It is intended that subject matter disclosed in any one portion herein can be combined with the subject matter of one or more other portions herein as long as such combinations are not mutually exclusive or inoperable. In addition, many variations, enhancements and modifications of the concepts described herein are possible.

The terms and descriptions used above are set forth by way of illustration only and are not meant as limitations. Those skilled in the art will recognize that many variations can be made to the details of the above-described embodiments without departing from the underlying principles of the invention.

The invention claimed is:

1. A flow diversion device comprising:
a generally tubular wire stent frame formed from a plurality of wire elements, each wire element in the plurality of wire elements having a zig-zag pattern shape, wherein at least one end of a first wire element in the plurality of wire elements is attached to at least one end of a second wire element adjacent to the first wire element to promote flexibility of the wire stent frame; and
a base layer attached to the wire stent frame and surrounding at least a portion thereof, the base layer formed of porous graft material having a plurality of perforations formed therethrough, the plurality of perforations comprising incisions that form flaps spaced apart on the base layer,
wherein the wire stent frame supports the base layer in an open condition,
wherein a proximal end and a distal end of the wire stent frame are open to allow blood to freely flow along a longitudinal axis of the wire stent frame, and
wherein the proximal end and the distal end are free of the base layer.

2. The flow diversion device of claim 1, wherein at least a second end of the adjacent first and second wire elements is free from attachment to promote flexibility of the wire stent frame.

3. The flow diversion device of claim 1, wherein the proximal end and the distal end of the wire stent frame further includes a radiopaque marker.

4. The flow diversion device of claim 1, further comprising a jacket attached to and surrounding the base layer.

5. The flow diversion device of claim 1, further comprising an anchor stent attached to the wire stent frame.

6. A delivery system including the flow diversion device of claim 1, the delivery system further comprising:
a guidewire detachably coupled to the proximal end or the distal end of the wire stent frame; and
a catheter for delivering the flow diversion device to a treatment location for an intracranial aneurysm.

7. A delivery system including the flow diversion device of claim 1, the delivery system further comprising a catheter carrying a flexible tube coupled to the proximal end of the wire stent frame, wherein the flexible tube is operable for delivering particles injected through the catheter, the particles traveling through the wire stent frame and into a lumen at which the wire stent frame is located.

8. A flow diversion device comprising:
a generally tubular wire stent frame formed from a plurality of wire elements, each wire element in the plurality of wire elements having a zig-zag pattern shape, wherein at least one end of a first wire element in the plurality of wire elements is attached to at least one end of a second wire element adjacent to the first wire element to promote flexibility of the wire stent frame; and
a base layer attached to the wire stent frame and surrounding at least a portion thereof, the base layer formed of porous graft material having a plurality of perforations formed therethrough, wherein the perforations comprise incisions that form flaps spaced apart on the base layer, wherein the wire stent frame supports the base layer in an open condition, and wherein the perforations enlarge or change shape with increased flow demand.

9. The flow diversion device of claim 8, wherein the incisions comprise half-circle incisions.

10. The flow diversion device of claim 8, wherein at least a second end of the adjacent first and second wire elements is free from attachment to promote flexibility of the wire stent frame.

11. The flow diversion device of claim 8, wherein a proximal and distal end of the wire stent frame further includes a radiopaque marker.

12. The flow diversion device of claim 8, wherein the wire elements at a distal end of the wire stent frame are attached to one another to form a closed, conically shaped structure at the distal end, and wherein the base layer is attached around the distal end of the wire stent frame.

13. The flow diversion device of claim 12, wherein the wire elements at a proximal end of the wire stent frame opposite the distal end are attached to one another to form a closed, conically shaped structure at the proximal end, and wherein the proximal end is free of the base layer.

14. The flow diversion device of claim 8, wherein the wire elements at a proximal end of the wire stent frame are attached to one another to form a closed, conically shaped structure at the proximal end, and wherein the base layer is attached around the proximal end of the wire stent frame.

15. The flow diversion device of claim 14, wherein the wire elements at a distal end of the wire stent frame are not attached to each other such that the distal end of the wire stent frame is open, wherein the distal end is further free of the base layer.

16. A delivery system including the flow diversion device of claim 14, the delivery system further comprising a catheter carrying a flexible tube coupled to the proximal end of the wire stent frame, wherein the flexible tube is operable for delivering particles injected through the catheter, the particles traveling through the wire stent frame and into a lumen at which the wire stent frame is located.

17. The flow diversion device of claim 8, further comprising a jacket attached to and surrounding the base layer.

18. The flow diversion device of claim 8, further comprising an anchor stent attached to the wire stent frame.

19. A delivery system including the flow diversion device of claim 8, the delivery system further comprising:
a guidewire detachably coupled to a proximal or distal end of the wire stent frame; and a catheter for delivering the flow diversion device to a treatment location for an intracranial aneurysm.

* * * * *